United States Patent
Noble et al.

(10) Patent No.: US 10,222,379 B2
(45) Date of Patent: Mar. 5, 2019

(54) DEVICES AND METHODS FOR MEASUREMENT OF SAMPLE PROPERTIES

(71) Applicant: EXACSYS LIMITED, London, Greater London (GB)

(72) Inventors: Michael Noble, Melbourn (GB); Simon Kew, Melbourn (GB); David Edington, Melbourn (GB); John Rippeth, Melbourn (GB); Mark Humphries, Melbourn (GB)

(73) Assignee: PA KNOWLEDGE LIMITED, London (GB)

( * ) Notice: Subject to any disclaimer, the term of this patent is extended or adjusted under 35 U.S.C. 154(b) by 431 days.

(21) Appl. No.: 14/427,446

(22) PCT Filed: Sep. 10, 2013

(86) PCT No.: PCT/GB2013/052362
§ 371 (c)(1),
(2) Date: Mar. 11, 2015

(87) PCT Pub. No.: WO2014/041339
PCT Pub. Date: Mar. 20, 2014

(65) Prior Publication Data
US 2015/0247862 A1    Sep. 3, 2015

(30) Foreign Application Priority Data
Sep. 11, 2012    (GB) .................. 1216163.4

(51) Int. Cl.
*G01N 33/543*    (2006.01)
*G01N 33/58*    (2006.01)
*G01N 33/558*    (2006.01)

(52) U.S. Cl.
CPC ....... *G01N 33/58* (2013.01); *G01N 33/54386* (2013.01); *G01N 33/558* (2013.01)

(58) Field of Classification Search
None
See application file for complete search history.

(56) References Cited

U.S. PATENT DOCUMENTS

| 5,710,005 A | 1/1998 | Rittenburg |
| 6,140,134 A | 10/2000 | Rittenburg |

(Continued)

FOREIGN PATENT DOCUMENTS

| WO | WO 98/18964 | 5/1998 |
| WO | WO 00/72020 | 11/2000 |

(Continued)

OTHER PUBLICATIONS

Nelson et al., Concentration Gradient Immunoassay 1. An Immunoassay Based on Interdiffusion and Surface Binding in a Microchannel, Analytical Chemistry, vol. 79, No. 10, published online Apr. 17, 2007. (Year: 2007).*

(Continued)

*Primary Examiner* — Rebecca L Martinez
(74) *Attorney, Agent, or Firm* — Nixon & Vanderhye P.C.

(57) ABSTRACT

The present invention provides a flexible format for diagnostic tests that is applicable to measuring a wide range of properties of fluids, particularly physiological fluids, by creating a concentration gradient of an indicator in the sample under analysis and measuring a flux of the indicator through the sample which is used to determine a property of the sample. Aspects of the invention include a method of testing a property of a physiological fluid in a portable test device, a portable test device and a kit including a portable test device and a processor.

26 Claims, 2 Drawing Sheets

(56) References Cited

U.S. PATENT DOCUMENTS

| | | |
|---|---|---|
| 2002/0090644 A1 | 7/2002 | Weigl et al. |
| 2003/0211507 A1 | 11/2003 | Hatch et al. |
| 2006/0155905 A1 | 7/2006 | Leino et al. |
| 2010/0296973 A1 | 11/2010 | Hefti et al. |
| 2013/0112573 A1 | 5/2013 | Noble et al. |

FOREIGN PATENT DOCUMENTS

| | | |
|---|---|---|
| WO | WO 03/091732 | 11/2003 |
| WO | WO 2011/138592 | 11/2011 |

OTHER PUBLICATIONS

International Search Report for PCT/GB2013/052362 dated Dec. 10, 2013, 4 pages.
Written Opinion of the International Searching Authority for PCT/GB2013/052362, dated Dec. 10, 2013, 6 pages.
Jun. 7, 2017 Communication pursuant to Article 94(3) EPC issued in European Application No. 13763275.8.
Afromowitz et al., "Microfluidic Chemical Analytical Systems," Paul Yager Research Group, Aug. 23, 1997, XP055377361, Retrieved on May 31, 2017 from http://faculty.washington.edu/yagerp/progressinmfcas.html.
Hatch et al., "A rapid diffusion immunoassay in a T-sensor," Nature Biotechnology, vol. 19, No. 5, May 2001, pp. 461-465, XP002303538.
Foley et al., "Concentration Gradient Immunoassay. 2. Computational Modeling for Analysis and Optimization," Analytical Chemistry, vol. 79, No. 10, May 2007 pp. 3549-3553, XP055236511.

\* cited by examiner

DEVICES AND METHODS FOR MEASUREMENT OF SAMPLE PROPERTIES

This application is the U.S. national phase of International Application No. PCT/GB2013/052362, filed 10 Sep. 2013, which designated the U.S. and claims priority to GB 1216163.4, filed 11 Sep. 2012, the entire contents of each of which are hereby incorporated by reference.

The present invention relates to devices and methods and kits for measurement of sample properties. It is particularly, but not exclusively, concerned with devices and methods for the measurement of properties of samples of physiological fluids.

Properties of physiological fluids can be indicative of the status of health of the individual from which the sample is derived. These properties include biophysical characteristics, for example plasma viscosity, blood viscosity, haematocrit (Hct) level and biochemical characteristics, such as the concentration of disease state indicating biomarkers and presence or absence of pathogenic agents. Moreover, there are properties of physiological fluids which can indicate a person's likely response to a therapy for instance, the proportion of a drug substance dose that remains free to exert its pharmacological action after the binding of a fraction of the dose by serum proteins. Personalized drug response knowledge of this kind could lead to individualized therapy, for example reducing dose where serum protein drug binding is low.

A diverse array of analytical methods has been developed to characterise these properties to help diagnose and manage patient health. These methods range from those conducted in a central laboratory setting by lab technicians, through "point of care" tests, conducted by a physician at the bedside to self-tests conducted by the patient himself. The importance of point of care tests and self-testing is rising as health systems around the world are becoming increasingly concerned with the management of chronic conditions, such as diabetes mellitus, Chronic Obstructive Pulmonary Disease (COPD) and heart disease. These conditions require long term care which is generally best, and most cost efficiently, delivered outside of the hospital in-patient setting.

Accordingly, there is a need for point of care and self-test methods and devices to determine properties of physiological fluids. Preferably such test should deliver accurate, precise and reliable results as well as being easy to operate and low cost. Currently there are few tests in routine use that meet all of these requirements.

The most prevalent example of self-test devices is Self-Monitoring of Blood Glucose (SMBG), which is used by people with diabetes to help manage their glycaemic level. Typical systems for SMBG comprise a meter and a disposable strip containing detection chemistry which together provide information on glucose levels in a blood sample. Although such devices are convenient and relatively low cost, the measurement accuracy of these systems has been called into question. For example, the US FDA convened a public meeting to explore blood glucose meter accuracy standards in March 2010. Despite his concern, SMBG is a useful tool in management of diabetes and is underpinned by a successful commercial model where manufacturers and healthcare payers have both benefited from the economies of scale that have become possible.

A further example is the monitoring of the blood clotting time by people on anticoagulant therapy as a way of monitoring (and therefore maintaining) the appropriate fluidity of their blood. Currently available systems for coagulation monitoring are expensive, both in terms of the meter and the disposable strips and are not as convenient and easy to use as SMBG systems. Arguably this has limited their uptake in many countries, despite the potential advantages for users.

Other properties of physiological fluids have been proposed as potentially valuable diagnostic tests, but have not been fully evaluated due to the absence of any reliable point of care or self-test device. One example of such a property is plasma viscosity, which is a non-specific indicator of disease and may be linked to a number of conditions including diabetes mellitus and heart disease (see Danesh et al, Eur. Heart Journal (2000) 21 515-520) but is conventionally measured using a capillary viscometer, requiring laboratory equipment and skill.

Other methods of direct measurement of physiological fluid properties suffer from the same issues of requiring any or all of complex kit, multiple steps and long time to result (for example a microhaematocrit centrifuge for haematocrit or extended time requirements or erythrocyte sedimentation rate). Methods to determine diffusivity of molecules in blood (and thereby infer parameters such as plasma viscosity, blood viscosity, osmolarity and Hct), typically require a flow cell type approach. This requires significant sample volume as well as complex instrumentation that is not feasible to use in the Point of Care setting (Nanne et al ASAIO J. (2010) 56, 151-156).

In US2002/090644, a method and device is disclosed for detecting analyte particles based on the interaction between the analyte particle and specific binding particles, where the altered diffusion rate of the bound complex indicates the presence of the analyte in the test sample. The requirement to provide binding particles means that this invention is limited to assays (for example immunoassays) where a specific target analyte is being detected and there is no possibility of characterising the biophysical properties of the test sample. The detection disclosed takes the form of an optical detection of the 'diffusion front' where interaction occurs. Moreover, the devices disclosed have two adjacent laminar flow fluid streams, one for the test sample itself and a further diffusion steam containing binding particles. The need for two adjacent flowing streams of fluid makes the test equipment complex, with an additional requirement for a pumping means and a means of storing the diffusion stream and waste fluid. Moreover, the overall sample volume requirement is increased since sample is flowing for the duration of the assay.

In US2006/115905 a method and device is disclosed for detecting the presence of analyte particles based on their diffusion into a hydrogel containing substantially immobilised binding particles and detecting the position of the analyte particles. This application similarly requires provision of binding particles limiting the scope of the assay method. In this method analyte in the test sample diffuses into the hydrogel where any binding reaction may take place. The requirement for sample to diffuse through the hydrogel slows diffusion with the effect of increasing test time and further limits the nature of the analyte particle to be a low molecular weight species since diffusion of larger molecules in the hydrogel phase would be very slow. Moreover, because biological samples such as blood may be viscous and contain cells and macromolecules that could accumulate at the interface between the hydrogel and the test sample, there is a likely requirement to dilute such test samples. Provision of a hydrogel layer is complex and costly and is required to maintain mechanical stability throughout the course of the assay.

Existing approaches to coagulation testing include those with relatively complex detection means where the mobility of iron particles under alternating magnetic fields is monitored optically. This requires several functions within the meter which contribute to a relatively high cost. Electrochemical based coagulation monitors exist, but these devices are significantly more expensive than SMBG technology. Alternative approaches to Point of Care coagulation testing are being investigated, including viscometry (e.g. by Microvisk Ltd) but again these appear to be significantly less convenient in terms of blood sample volume requirement than SMBG technology.

So called 'lab-on-a-chip' based approaches to diagnostic assays generally utilise micro-fabrication technologies to recreate multiple process step assays in a miniature format. The complexity of the Lab-on-a-chip approach appears to have been one of the reasons that this class of devices has not made the commercial progress initially envisaged.

Lateral flow type immunoassays have, by contrast, had significant uptake and are used in a variety of applications. These tests are not as convenient for users as SMBG tests and are of higher cost. Moreover, immunoassays are limited to binding assays, rather than the broader range of blood properties that may be desired.

Accordingly the present invention seeks to provide methods and devices which provide a platform for point of care and self-testing that is low cost, accurate and easy to use, preferably requiring a small sample volume and can be used for determining a number of different properties of physiological fluids.

At their broadest, aspects of the present invention provide a flexible format for diagnostic tests that is applicable to measuring a wide range of properties of fluids, particularly physiological fluids, by creating a concentration gradient of an indicator in the sample under analysis and measuring flux of the indicator through the sample which is preferably used to determine a property of the sample.

A first aspect of the present invention provides a method of testing, in a portable device, a property of a physiological fluid, the method including the steps of: introducing a sample of said fluid to said device; creating a concentration gradient across said sample between either: a) a source of a predetermined amount of an indicator or b) an indicator formed as a reaction product of an indicator precursor and the fluid, and a detector; measuring the flux of said indicator at the detector; and determining said property of the physiological fluid from said measurement of the flux.

The determination may be made by determining the time at which the indicator first arrives at the detector, or by which a particular amount of the indicator has arrived at the detector, compared to a reference point, or from the rate of arrival of the indicator or the change in the rate of arrival over time. Information from other sources (such as a measurement of the temperature) may also be used in determining the property of the fluid from the measured flux.

The concentration gradient created in the device may be between a source of a predetermined amount of indicator, for example, included in the device during its manufacturing, or may be generated when the fluid is introduced into the device as a result of a reaction between an indicator precursor (which, again, may be included in the device during its manufacturing) and one or more components of the fluid.

In certain embodiments, the property to be determined is the concentration of a particular analyte in the fluid and the indicator is chosen to have specific affinity for that analyte, for example an anticipated interaction (e.g. a specific binding reaction) with one or more target compounds in the sample. In this case, any binding between the indicator and the target molecule would influence flow through the sample. In some embodiments this may be a binding reaction between an indicator antibody and a target antigen. Alternatively, the transient binding of an enzyme and its substrate could be used in this context. The measured flux would then provide information about the presence and/or quantity of the target compound in the sample.

In other embodiments the indicator is chosen on the basis of expected interaction with components in the sample where the interaction is not a specific binding, but an equilibration based on relative polarity or ionic charge of the indicator molecule and the target component. For example an lipophilic indicator molecule would preferentially partition into a lipid component of the sample such that its net progress through the aqueous part of the sample is retarded (measured as a reduced flux at the detector) thereby imparting information about the lipid composition in the sample.

In other embodiments the property to be determined is an inherent property of the fluid and the indicator is chosen so as to have no affinity for any components which are likely to be present in the fluid being tested. The indicator would then be a passive indicator of a biophysical property of the sample where the rate of passage of the indicator molecule through the analysed sample can be used to quantify properties of the sample such as viscosity or presence of components, such as red blood cells or structures composed thereof, that hinder flux by increasing the effective diffusion distance (as the indicator has to 'travel' around the obstacle).

In certain embodiments, the indicator precursor could be a chemical species that is transformed by a chemical reaction with a component naturally present in the test fluid. For example the enzyme alkaline phosphatase in the test fluid could dephosphorylate a substrate such as N-ferrocenyl-4-aminophenyl-phosphate (the indicator precursor) forming the indicator ferrocene.

In other embodiments, the indicator species may be consumed by a reaction with a component the test sample. For example if the indicator is NADP+, its conversion to NADPH by G6PDH in a blood sample would reduce the flux of the indicator to the detector. In these embodiments, the flux measured at the detector is related to the amount or activity of the consuming or transforming component in the test sample.

Preferably the fluid is introduced into a sample chamber within the device by capillary action. This provides for automatic, accurate and complete filling of the chamber with the physiological fluid.

Preferably the sample is substantially or entirely static during the measurement of the flux of the indicator. In particular, the sample generally does not need to flow, but there could be some fluidic movement of the sample without affecting the results obtained. This means that a lower overall sample volume is generally required compared to methods and devices in which fluid flow streams are analysed, and the required amount of indicator is minimised.

The volume of sample fluid required for testing is preferably 5 µL or less, more preferably 2 µL or less and still more preferably 1 µL or less.

Preferably the sample is not processed prior to introducing the sample to said device. This means that there is no need for any sample preparation and so the method can be used by an individual who does not have detailed training in the preparation of samples for analysis. Moreover, the method is easier and quicker to use and there is less possibility of contamination or interference from, for example, environmental factors.

In certain embodiments, the portable device further includes a plurality of detectors at different locations in the device and the method further includes the step of measuring the flux of said indicator at said plurality of locations.

This arrangement enables independent measurements of the indicator flux at different positions in the sample chamber and therefore can provide spatially resolved information regarding the properties of the physiological fluid.

For example, it may enable the detection of inhomogeneity in the test sample, for example due to the presence of a forming or formed blood clot as the indicator may arrive at different detectors at different times or at different rates.

Additionally, the use of a plurality of indicator and detector combinations may enable multiple parameters of the test fluid to be derived. These parameters could be used to provide independent measurements or could be used in combination to derive a subset of measures.

In certain embodiments the detection system may influence the diffusion of the indicator species. For example an electrochemical detector system could create an electric field affecting flux of a charged molecule to the surface. The flux to a detector under the influence of an electric field could be compared to the flux to a different detector where a field is not applied. Alternatively, flux of an indicator to a detector under different conditions (for example test sample temperature) could provide information on test sample properties.

In certain embodiments the source of said indicator is arranged such that each detector is a different distance from said source and the measurements of the flux are measured through different amounts of the sample.

This allows independent measurement of indicator flux at several different (and known) distances from the source. This may allow further or more detailed information about properties of the fluid to be determined.

In certain embodiments there are multiple sources of said indicator arranged at different locations in the chamber.

This configuration may alternatively or additionally allow further or more detailed information about properties of the fluid to be determined.

In certain embodiments there is a plurality of different indicators and the step of measuring includes measuring the flux of each of said indicators at a detector.

The different indicators may be arranged in such a way that each mixes with the sample fluid to set a concentration gradient across the sample at a different time. For example, the indicators may be arranged in a series of successive layers such that the layer furthest from the sample (and closest to the underlying substrate) is accessed by the sample fluid after the layer that is in immediate contact with it. Such layers are relatively simple to manufacture by, for example, a repeated printing process. In this configuration the sample properties could be derived from either the differential time to access the different sample layers or the different fluxes across the sample or a combination of these effects.

In certain embodiments indicators could be arranged in combination with reagent components. For example the blood clotting agent thromboplastin could be arranged in combination with an indicator such as glucose. The arrangement of the indicator and reagents could be co-located (for example as part of the same formulation); spatially distinct (separate locations in the chamber); or arranged so as to be temporally distinct in their interaction with the test sample by being placed in successive layers in the same location or a combination of these three possibilities.

The combination of spatial and temporal exposure of reagents and indicators to the test sample enables a wide range of assay types to be devised using this simple, low cost format.

The step of determining may use the measurement of the flux of the plurality of different indicators to determine a single property of the physiological fluid. This may enable a more accurate determination of that property. For example, the indicators may be chosen as substances which have different diffusivities through the sample and the measured flux of each indicator compared to an expected ratio between the indicators to provide for internal calibration or confirmation of the determined property.

Alternatively or additionally the step of determining may use the measurement of the flux of the plurality of different indicators to determine a plurality of properties of the physiological fluid. This enables more than one property to be determined from a single sample of the physiological fluid and therefore reduces the number of times a sample has to be taken. In certain cases it may be desirable to measure more than one property in a single sample so that the relationship between the properties can be assessed.

In certain embodiments the chamber further includes a layer covering the source of the indicator, said layer being arranged to interact with a component in the sample to be tested prior to release of the indicator into the sample.

In such embodiments, the transport of the indicator may only take place once the layer has been modified by interaction with a component in the sample. For example, the modulation could occur by enzyme catalysed hydrolysis, or a binding event, osmolarity (an indicator of dehydration) or pH change (for example as an indication of severe sepsis) causing change in structure.

Embodiments of the above first aspect can include some, all or none of the optional or preferred features set out. Preferably the method of this aspect is used in conjunction with a device according to the second aspect below or a kit according to the third aspect below, but this is not essential.

A second aspect of the present invention provides a portable test device for determining a property of a physiological fluid, the test device having: a sample chamber for receiving a sample of the physiological fluid; and, arranged at different locations in the chamber, a source of either: a predetermined amount of an indicator; or of an indicator precursor; and a detector arranged to measure the flux of said indicator either from the source or from a reaction between said indicator precursor and the fluid, such that when the fluid is present in said chamber, a concentration gradient of the indicator is created across said fluid between the source and the detector and the detector measures the flux of said indicator through said fluid, said flux being used to determine the property of the fluid.

The determination may be made by determining the time at which the indicator first arrives at the detector, or by which a particular amount of the indicator has arrived at the detector, compared to a reference point, or from the rate of arrival of the indicator or the change in the rate of arrival over time. Information from other sources (such as a measurement of the temperature from a temperature sensor) may also be used in determining the property of the fluid from the measured flux.

The concentration gradient created in the device may be between a source of a predetermined amount of indicator, for example, included in the device during its manufacturing, or may be generated when the fluid is introduced into the device as a result of a reaction between an indicator precursor (which, again, may be included in the device during its manufacturing) and one or more components of the fluid.

In certain embodiments, the property to be determined is the concentration of a particular analyte in the fluid and the indicator is chosen to have specific affinity for that analyte, for example an anticipated specific binding reaction with one or more target compounds in the sample. In this case, any binding between the indicator and the target molecule would influence flow through the sample. In some embodiments this may be a binding reaction between an indicator antibody and a target antigen. Alternatively, the transient binding of an enzyme and its substrate could be used in this context. The measured flux would then provide information about the presence and/or quantity of the target compound in the sample.

In other embodiments the indicator is chosen on the basis of expected interaction with components in the sample where the interaction is not a specific binding, but an equilibration based on relative polarity or ionic charge of the indicator molecule and the target component. For example an lipophilic indicator molecule would preferentially partition into a lipid component of the sample such that its net progress through the aqueous part of the sample is retarded (measured as a reduced flux at the detector) thereby imparting information about the lipid composition in the sample.

In other embodiments the property to be determined is an inherent property of the fluid and the indicator is chosen so as to have no affinity for any components which are likely to be present in the fluid being tested. The indicator would then be a passive indicator of a biophysical property of the sample where the rate of passage of the indicator molecule through the analysed sample can be used to determine properties of the sample such as viscosity.

In certain embodiments the indicator is arranged on part of the interior surface of the chamber, for example as a surface coating. This may facilitate simple manufacture as the indicator can be layered (e.g. by printing) onto one component before assembly to the main body of the device.

Preferably the device is arranged to draw fluid into the chamber by capillary action. This provides for automatic, accurate and complete filling of the chamber with the physiological fluid.

The portable test device may have a processor which is arranged to produce a reading of the property of the fluid from the flux detected by the detector. Alternatively the portable test device may provide outputs which are related to the flux of indicator detected by the detectors to a processor which is removably attached to the test device.

In certain embodiments, the indicator precursor could be a chemical species that is transformed by a chemical reaction with a component naturally present in the test fluid. For example the enzyme alkaline phosphatase in the test fluid could dephosphorylate a substrate such as N-ferrocenyl-4-aminophenyl-phosphate (the indicator precursor) forming the indicator ferrocene.

In other embodiments, the indicator species may be consumed by a reaction with a component the test sample. For example if the indicator is NADP+, its conversion to NADPH by G6PDH in a blood sample would reduce the flux of the indicator to the detector. In these embodiments, the flux measured at the detector is related to the amount or activity of the consuming or transforming component in the test sample.

Preferably the sample is substantially or entirely static during the measurement of the flux of the indicator. In particular, the sample generally does not need to flow, but there could be some fluidic movement of the sample without affecting the results obtained. This means that a lower overall sample volume and indicator amount is generally required compared to methods and devices in which fluid flow streams are analysed.

Preferably the volume of the chamber (and therefore the volume of fluid sample required) is 5 μL or less, more preferably 2 μL or less and still more preferably 1 μL or less.

In certain embodiments, the device has a plurality of detectors located at different locations in the chamber, each arranged to measure the flux of said indicator from the source.

This arrangement enables independent measurements of the indicator flux at different positions in the sample chamber and therefore provide spatially resolved information regarding the properties of the physiological fluid.

For example, it may enable the detection of inhomogeneity in the test sample, for example due to the presence of a forming or formed blood clot as the indicator may arrive at different detectors at different times or at different rates.

In certain embodiments the source of said indicator is arranged such that each detector is a different distance from said source and the measurements of the flux are measured through different amounts of the sample.

This allows independent measurement of indicator flux at several different (and known) distances from the source. This may allow further or more detailed information about properties of the fluid to be determined.

In certain embodiments there are multiple sources of said indicator arranged at different locations in the chamber.

This configuration may alternatively or additionally allow further or more de ailed information about properties of the fluid to be determined.

In certain embodiments the source or the plurality of sources includes a plurality of different indicators and at least one detector is arranged to measure the flux of each of said indicators. A single detector may be provided which is adapted to measure the flux of each of the indicators, or separate detectors may be provided for each of the indicators.

The different indicators may be arranged in such a way that each mixes with the sample fluid to set a concentration gradient across the sample at a different time. For example, the indicators may be arranged in a series of successive layers such that the layer furthest from the sample (and closest to the underlying substrate) is accessed by the sample fluid after the layer that is in immediate contact with it. Such layers are relatively simple to manufacture by, for example, a repeated printing process. In this configuration the sample properties could be derived from either the differential time to access the different sample layers or the different fluxes across the sample or a combination of these effects.

In certain embodiments indicators could be deposited inside the sample chamber in combination with reagent components. For example the blood clotting agent thromboplastin could be deposited in the chamber in combination with an indicator such as glucose. The arrangement of the indicator and reagents could be co-located (for example as part of the same formulation); spatially distinct (separate locations in the chamber); or arranged so as to be temporally distinct in their interaction with the test sample by being placed in successive layers in the same location—or a combination of these three possibilities.

The combination of spatial and temporal exposure of reagents and indicators to the test sample enables a wide range of assay types to be devised using this simple, low cost format.

The measured flux of the plurality of different indicators may be used to determine a single property of the physiological fluid. This may enable a more accurate determination of that property. For example, the indicators may be chosen as substances which have different diffusivities through the sample and the measured flux of each indicator compared to an expected ratio between the indicators to provide for internal calibration or confirmation of the determined property.

Alternatively or additionally the measured flux of the plurality of different indicators may be used to determine a plurality of properties of the physiological fluid. This enables more than one property to be determined from a single sample of the physiological fluid and therefore reduces the number of times a sample has to be taken. In certain cases it may be desirable to measure more than one property in a single sample so that the relationship between the properties can be assessed.

In certain embodiments, the chamber further includes a layer covering the source of the indicator, said layer being arranged to interact with a component in the sample to be tested prior to release of the indicator into the sample.

In such embodiments, the transport of the indicator may only take place once the layer has been modified by interaction with a component in the sample. For example, the modification could occur by enzyme catalysed hydrolysis, or a binding event, osmolarity (an indicator of dehydration) or pH change (for example as an indication of severe sepsis) causing change in structure.

Embodiments of the above second aspect can include some, all or none of the optional or preferred features set out. Preferably the device of this aspect is used in conjunction with a method according to the above first aspect, but this is not essential.

A third aspect of the present invention provides a kit for determining a property of a physiological fluid, the kit comprising: a portable test device, the test device having: a sample chamber for receiving a sample of the physiological fluid; and, arranged at different locations in the chamber, a source of either: a predetermined amount of an indicator, or of an indicator precursor; and a detector arranged to measure the flux of said indicator either from the source or from a reaction between said indicator precursor and the fluid, such that when the fluid is present in said chamber, a concentration gradient of the indicator is created across said fluid between the source and the detector and the detector measures the flux of said indicator through said fluid; and the kit also having a processor for determining a property of the fluid from the measurement of said flux.

The determination may be made by determining the time at which the indicator first arrives at the detector, or by which a particular amount of the indicator has arrived at the detector, compared to a reference point, or from the rate of arrival of the indicator or the change in the rate of arrival over time. Information from other sources (such as a measurement of the temperature from a temperature sensor) may also be used in determining the property of the fluid from the measured flux.

The concentration gradient created in the device may be between a source of a predetermined amount of indicator, for example, included in the device during its manufacturing, or may be generated when the fluid is introduced into the device as a result of a reaction between an indicator precursor (which, again, may be included in the device during its manufacturing) and one or more components of the fluid.

In certain embodiments, the property to be determined is the concentration of a particular analyte in the fluid and the indicator is chosen to have specific affinity for that analyte, for example an anticipated specific binding reaction with one or more target compounds in the sample. In this case, any binding between the indicator and the target molecule would influence flow through the sample. In some embodiments this may be a binding reaction between an indicator antibody and a target antigen. Alternatively, the transient binding of an enzyme and its substrate could be used in this context. The measured flux would then provide information about the presence and/or quantity of the target compound in the sample.

In other embodiments the indicator is chosen on the basis of expected interaction with components in the sample where the interaction is not a specific binding, but an equilibration based on relative polarity or ionic charge of the indicator molecule and the target component. For example an lipophilic indicator molecule would preferentially partition into a lipid component of the sample such that its net progress through the aqueous part of the sample is retarded (measured as a reduced flux at the detector) thereby imparting information about the lipid composition in the sample.

In other embodiments the property to be determined is an inherent property of the fluid and the indicator is chosen so as to have no affinity for any components which are likely to be present in the fluid being tested. The indicator would then be a passive indicator of a biophysical property of the sample where the rate of passage of the indicator molecule through the analysed sample can be used to determine properties of the sample such as viscosity.

The indicator may be arranged on part of the interior surface of the chamber, for example as a surface coating. This may facilitate simple manufacture as the indicator can be layered (e.g. by printing) onto one component before assembly to the main body of the device.

In certain embodiments, the indicator precursor could be a chemical species that is transformed by a chemical reaction with a component naturally present in the test fluid. For example the enzyme alkaline phosphatase in the test fluid could dephosphorylate a substrate such as N-ferrocenyl-4-aminophenyl-phosphate (the indicator precursor) forming the indicator ferrocene.

In other embodiments, the indicator species may be consumed by a reaction with a component the test sample. For example if the indicator is NADP+, its conversion to NADPH by G6PDH in a blood sample would reduce the flux of the indicator to the detector. In these embodiments, the flux measured at the detector is related to the amount or activity of the consuming or transforming component in the test sample.

Preferably the device is arranged to draw fluid into the chamber by capillary action. This provides for automatic, accurate and complete filling of the chamber with the physiological fluid.

Preferably the sample is substantially or entirely static during the measurement of the flux of the indicator. In particular, the sample generally does not need to flow, but there could be some fluidic movement of the sample without affecting the results obtained. This means that a lower overall sample volume is generally required compared to methods and devices in which fluid flow streams are analysed.

In certain embodiments the device has a plurality of detectors located at different locations in the chamber, each arranged to measure the flux of said indicator from the source and the processor is further arranged to determine a property of the fluid from comparison of the measurement of said flux at said plurality of detectors.

This arrangement enables independent measurements of the indicator flux at different positions in the sample chamber and therefore provide spatially resolved information regarding the properties of the physiological fluid.

For example, it may enable the processor to detect inhomogeneity in the test sample, for example due to the presence of a forming or formed blood clot as the indicator may arrive at different detectors at different times or at different rates.

In certain embodiments the source of said indicator is arranged such that each detector is a different distance from said source and the measurements of the flux are measured through different amounts of the sample.

This allows independent measurement of indicator flux at several different (and known) distances from the source. This may allow further or more detailed information about properties of the fluid to be determined. For example, determination of the flux at two different distances from the source could be used to more accurately determine apparent diffusivity of the indicator in the sample fluid since flux at a point remote from the source is highly dependent on the time/distance profile.

In certain embodiments there are multiple sources of said indicator arranged at different locations in the chamber.

This configuration may alternatively or additionally allow further or more detailed information about properties of the fluid to be determined.

In certain embodiments, the source or sources include a plurality of different indicators and at least one detector is arranged to measure the flux of each of said indicators.

The different indicators may be arranged in such a way that each mixes with the sample fluid to set a concentration gradient across the sample at a different time. For example, the indicators may be arranged in a series of successive layers such that the layer furthest from the sample (and closest to the underlying substrate) is accessed by the sample fluid after the layer that is in immediate contact with it. Such layers are relatively simple to manufacture by, for example, a repeated printing process. In this configuration the sample properties could be derived from either the differential time to access the different sample layers or the different fluxes across the sample or a combination of these effects.

In certain embodiments indicators could be deposited inside the sample chamber in combination with reagent components. For example the blood clotting agent thromboplastin could be deposited in the chamber in combination with an indicator such as glucose. The arrangement of the indicator and reagents could be co-located (for example as part of the same formulation); spatially distinct (separate locations in the chamber); or arranged so as to be temporally distinct in their interaction with the test sample by being placed in successive layers in the same location or a combination of these three possibilities.

The combination of spatial and temporal exposure of reagents and indicators to the test sample enables a wide range of assay types to be devised using this simple, low cost format.

The processor may be arranged to determine a single property of the physiological fluid from the measurement of the flux of the plurality of different indicators. This may enable a more accurate determination of that property. For example, the indicators may be chosen as species which have different diffusivities through the sample and the measured flux of each indicator compared to an expected ratio between the indicators to provide for internal calibration or confirmation of the determined property.

Alternatively or additionally, the processor may be arranged to determine a plurality of properties of the physiological fluid from the measurement of the flux of the plurality of different indicators. This enables more than one property to be determined from a single sample of the physiological fluid and therefore reduces the number of times a sample has to be taken. In certain cases it may be desirable to measure more than one property in a single sample so that the relationship between the properties can be assessed.

In certain embodiments the chamber further includes a layer covering the source of the indicator, said layer being arranged to interact with a component in the sample to be tested prior to release of the indicator into the sample.

In such embodiments, the transport of the indicator may only take place once the layer has been modified by interaction with a component in the sample. For example, the modulation could occur by enzyme catalysed hydrolysis, for example by lysozyme or amylase catalysed degradation of chitosan or hyaluronan layers, or a binding event, osmolarity (an indicator of dehydration) or pH change (an indication of severe sepsis) causing change in structure.

Embodiments of the above third aspect can include some, all or none of the optional or preferred features set out. Preferably the kit of this aspect is used in conjunction with a method of the first aspect above, but this is not essential.

Further aspects of the present invention provide methods, test devices and kits in which the measured flux of the indicator is used to determine information about the construction of the sample chamber rather than a property of the physiological fluid as set out in the above aspects. The other features of these aspects are otherwise as set out in the respect first, second or third aspect above, including some, all or none of the optional or preferred features set out in those aspects.

For example the height of the test chamber could be determined by measuring the relative flux at detectors on the opposing surface directly opposite the source and at a lateral distance from the source. Since the distance between the two detectors on the same surface is known and constant the ratio of flux of indicator at these detectors at a given time will be dependent on the distance between the detector surface and the surface coated with indicator, in other words the channel height. Characterisation of sample chamber dimensions in this way can then be used in interpreting information about test sample properties, for example as measured by other indicator species in the test device.

In all of the above aspects, the physiological fluid can be any fluid found in the human or animal body (in particular blood, but also including serum, plasma, saliva, urine, interstitial, wound fluid and/or intra-cellular fluid).

The indicators in each of the above embodiments may be selected from molecular species, particles or conjugates comprising particles and molecules. The indicator may be soluble in the intended sample medium or insoluble, provided that it is freely transportable through the test sample matrix. The indicator may be held in suitable formulation to enable diffusion on contact with the test sample. For example the formulation may be soluble or degradable on contact with the test sample to release the indicator. Alternatively an insoluble, physically intact formulation may allow flow of sample through it to dissolve or dislodge the indicator.

There may be one or more indicators with specific responsive detectors arranged to detect their diffusion through the test sample as appropriate. Indicators may be mixed and co-deposited in a continuous location (for example two indicators mixed in a film coating) or in one or more discrete locations (for example a series of dots making up a pattern). Alternately, different indicators may be located separately from each other in known positions with the test chamber.

In addition to having the advantage of widespread applicability, the methods and devices outlined in the aspects above have significant advantages when compared to existing diagnostic test methods in isolation.

Preferably embodiments of the present invention provide formats for conducting a range of analyses on physiological samples in a low cost way. Many of the embodiments of the present invention can be made by re-utilising elements of existing low cost, commercially accepted technology (particularly SMBG technology). However; the methods, devices and kits of the present invention preferably enable extension of the physical attributes of SMBG technology into numerous other application areas and further potential device formats.

Embodiments of the invention will now be described by way of example with reference to the accompanying drawings in which:

FIG. 1 shows, in schematic form, the configuration in a sample chamber of a test device according to an embodiment of the present invention.

Figure 1:
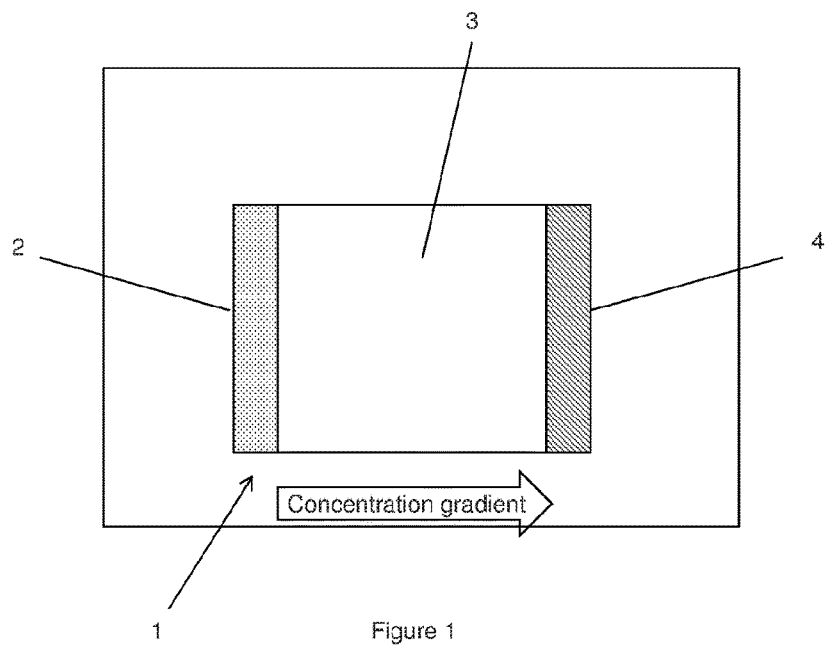
FIG. 1 shows, in schematic form, the configuration of a sample chamber forming part of a test device according to an embodiment of the present invention.

In the sample chamber 1, a concentration gradient is set up by having deposited on one side of the reaction chamber an indicator 2. The concentration gradient causes the indicator to be transported through the blood sample 3 (e.g. by diffusion) to a detector 4 on the opposite side of the chamber.

The indicator 2 can be selected from a wide range of possible indicators as previously discussed.

The indicator can be a passive indicator of a biophysical properly of the sample where the rate of passage of the indicator molecule through the analysed sample can be used to determine properties of the sample. For example, in a blood sample, this measurement could be used to determine properties such as plasma viscosity and haematocrit (Hct).

Alternatively, the indicator can be chosen on the basis of an expected interaction with components in the sample. For example an amphiphilic indicator molecule would reversibly partition into, or bind to, a lipid component of the sample, retarding its net progress through the sample (measured as a reduced flux at the detector) and thereby imparting information about the lipid composition in the sample. Example indicator molecules for this purpose are N-Alkylferrocenecarboxamide compounds which have been synthesised with variable length alkyl groups (CnFc with n 12, 14, 16) (see Kang et al J. Phys. Chem. B 2000, 104, 2082-2089).

A further example of an indicator molecule is one which has an affinity (e.g. an anticipated specific binding reaction) for target compounds in the sample. In this case, any binding between the indicator and the target molecule would influence flow through the sample. The measured rate of diffusion through the sample would in this case provide information about the presence and/or quantity of a target compound or particular property of the sample. For example, the binding of a drug compound, which is arranged to be the indicator, to human serum albumin, lipoprotein, glycoprotein and/or globulins in blood could be determined in this way.

Different schemes for interrogating a sample are included within the embodiments of the invention. For example the sample could be mixed with a specific binding agent, such as an antibody or aptamer, before introduction to the analysis chamber. In this instance the indicator molecule that dissolves and diffuses through the sample (and which would be labelled in such a way that it is detectable and distinctive from the target analyte) has an affinity for the (antibody/aptamer) binding agent, and would compete with any target analyte in the sample. If the target analyte is present in the sample at high concentration, there will be limited binding of the indicator molecule to the antibody and the passage of the indicator would be relatively unimpeded.

Mixing of the sample with the binding agent could take place in the analysis chamber or outside of it. Where mixing is inside the analysis chamber, the binding agent could be provided by dissolution of a predeposited layer or coating. One possible arrangement is to have the binding agent present on the side of the chamber opposite the indicator such that diffusion away from each surface enables the respective molecules or particles to meet and interact. In another embodiment, the binding agent could be deposited on a side or end wall. In further embodiments, the binding agent could be deposited in a layer on top of the indicator or co-formulated with the indicator. Where the mixing is outside of the analysis chamber, this could be achieved with a discrete mixing step (potentially utilising specific apparatus), or by mixing upstream of the analysis chamber in the same fluidic path.

A variety of schemes for detecting antibody (and other binding agent) targets are well known, but these generally have the disadvantage that they require a wash step to remove the unbound fraction. In the current invention, the need for a wash step is obviated by the concentration gradient which gives rise to an expected flux through to the detector in the absence of any binding, and an altered flux profile if binding or other interactions occur.

A further example of this type of arrangement is where a physiological sample suspected of bacterial infection is mixed with a porogenic antibiotic agent such as valinomycin, mellitin, magainin or polymyixin prior prior to analysis in the sample chamber. In this instance, the indicator molecule has the ability to enter into pores made in the bacterial cell wall by the antibiotic and so the diffusion path is significantly impacted, causing a delayed flux to the detector region.

Figures 2A, 2B:
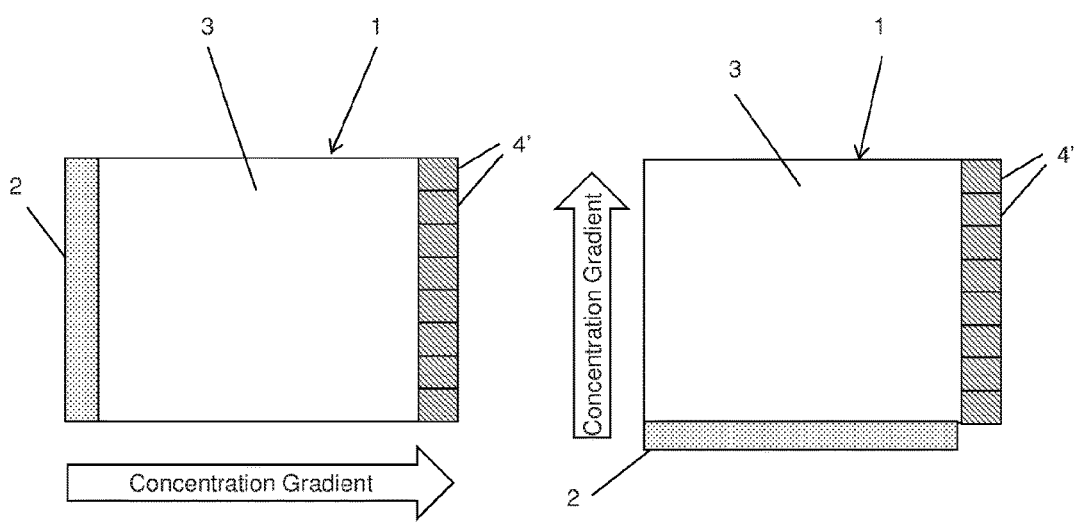
FIGS. 2a and 2b show, in schematic form, the configuration of sample chambers forming part of test devices according to further embodiments of the present invention.

In an alternative sample chamber of a test device according to a further embodiment of the present invention, as shown in FIG. 2a, multiple discrete detector means 4' are provided on the opposite side of the chamber 1 to the indicator 2, allowing independent measurements of indicator flux to be made at different positions within the sample chamber 1. This provides a device which can produce spatially resolved information on the properties of the physiological fluid in the sample chamber 1. This arrangement may enable the detection of inhomogeneity in the test sample, for example due to the presence of a forming or formed clot or structures such as rouleaux in the blood sample or could disclose whether the test chamber is completely filled.

In a modification of this embodiment, as shown in FIG. 2b, the source of the indicator 2 is positioned orthogonal to the array of detector means 4', such that each detector 4' measures indicator flux at a different distance from the indicator 2. This arrangement enables measurement of the progress of the indicator through the test sample matrix and may again indicate the presence of inhomogeneity in the test sample.

Figure 3:
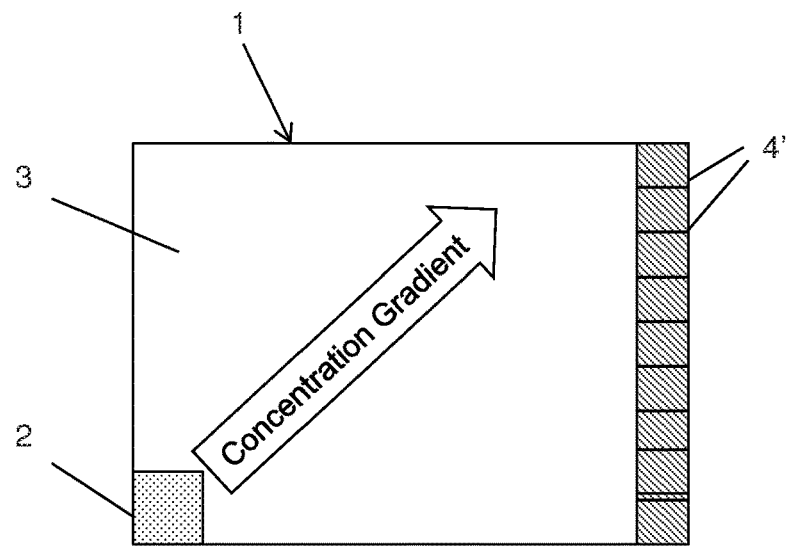
FIG. 3 shows, in schematic form, the configuration of a sample chamber forming part of a test device according to an embodiment of the present invention.

In a further alternative sample chamber of a test device according to a further embodiment of the present invention, shown in FIG. 3, a small source (approximating a point source) of an indicator 2 is positioned on the opposite side of the sample chamber 1 from a row of detectors 4', directly opposite the endmost detector 4a. This embodiment allows independent measurement of indicator flux at several different (and known) distances from the source.

Figure 4:
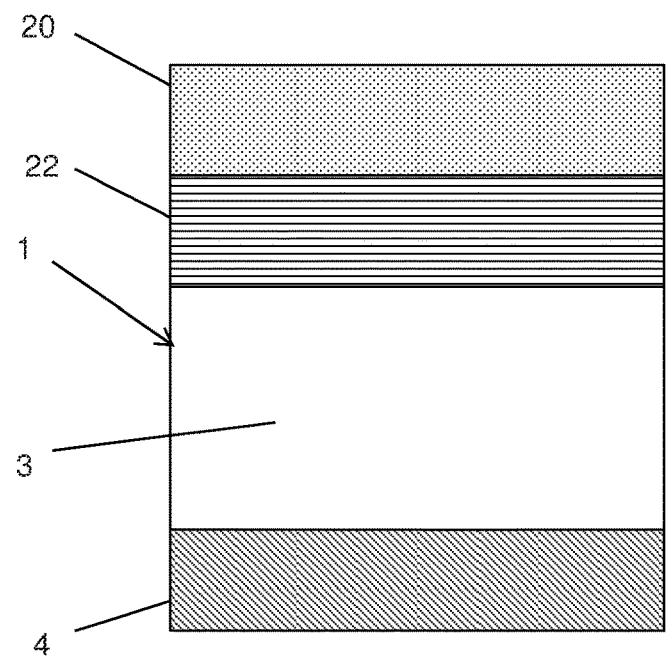
FIG. 4 shows, in schematic form, the configuration of a sample chamber forming part of a test device according to an embodiment of the present invention.

In a further embodiment, the indicator molecule could be contained within a layer that is separated from the sample by a covering layer. An example of such an arrangement is shown schematically in FIG. 4. The soluble indicator analyte 20 is covered by a receptor or membrane layer 22 which sits between the analyte 20 and the sample 3 and modulates the transport of the indicator to the sample chamber 1 and so to the detector 4.

In this embodiment, the transport (e.g. dissolution and subsequent diffusion) of the indicator molecule 20 can only take place once the covering layer 22 has been modified by interaction with a component in the test sample 3. Depending on the composition of the covering layer, the modulation could occur by enzyme catalysed hydrolysis, or a binding event, osmolarity (an indicator of dehydration) or pH change (for example as an indication of severe sepsis) causing change in structure.

The indicator 20 can be chosen by considering the property of the physiological sample being investigated, and the ability to measure its flux at the opposing detector surface 4. Where biophysical properties such as plasma viscosity and Hct are being measured in the sample, the indicator molecule can be any species whose diffusion through the test sample takes place in an acceptable test time and is easily detectable. Glucose is one such indicator molecule that could be used in this example, and this would have the advantage that low cost detector systems based on amperometric measurement of an enzyme catalysed oxidation reaction are already highly developed for SMBG purposes.

Alternatively, an indicator could be chosen where the species is directly oxidised (without an enzyme catalysed reaction) at the opposing electrode. Examples include methylene blue, ferrocene (and other metallocenes), ferrocyanide, 2-nitro acridone, Hexachlororuthenium, quinones, osmium complexes [Os(2,2'-bipyridyl)2LL'] and [Os(4,4'-dimethyl-2,2'-bipyridyl)2LL'], tetrathiofuvoline, hexamine ruthenium, and ascorbate. This choice of indicator would also benefit from the ability to substantially use the well-developed SMBG systems, and may have the further advantage of being lower cost since the use of expensive enzyme-based reagents systems is not required.

In arrangements in which the assay is intended to determine the effect of interaction of the indicator with a component of the test sample, the indicator molecule is chosen to display the appropriate affinity for that component of the test sample. For example a test device having an arrangement based on the affinity of biotin for avidin/streptavidin could be employed. Partitioning between lipid components and the aqueous phase in blood could be detected by measuring apparent diffusion of an indicator molecule such as ferulic acid through the test sample (Castelluccio et al Biochem. J. (1996) 316, 691-694). The indicator is not limited to being a molecule, but could be a particle or composite of the two. Such arrangements could be set up in an analogous way to that in which particles are used in multiple-particle tracking experiments (with video microscopy imaging) to determine microstructure of biological fluids (Crocker & Hoffman, Methods in Cell Biology, 83, 2007, pages 141-178.)

Further arrangements for altering molecules and particles to render them detectable by electrochemical, optical and other detection systems are well known and are not exhaustively enumerated here. They include both methods suited for low-cost point-of-care sensors and those used in clinical chemistry and in vitro diagnostic laboratories. Examples of such approaches include: optical methods (absorption; transmission, fluorescence, luminescence; colorimetry, surface plasmon resonance spectroscopy, attenuated total internal reflectance, leaky waveguide sensors, surface enhanced resonant raman spectroscopy, confocal fluorescence); acoustic methods (quartz crystal microbalance); electrical electrochemical (capacitance, amperometric, potentiometric, AC impedance, coulometric, magnetic, conductance, inductance).

For the concentration gradient method disclosed here, control of the distance or distances between indicator source and detector means will be an important aspect of the performance of the system. For example, implementation of the method in a format similar to current SMBG strips might place the indicator source on the lid of the capillary, with detector means on the base.

In these systems, the distance between capillary lid and the detection means is typically 100-150 μm, with this distance being defined by the height of the capillary walls. In embodiments of the present invention, this distance may be modified to achieve a desired degree of diffusional interaction of indicator with the sample and to optimise the time to result. For instance, increasing the capillary height to 200 μm will increase the time required for the indicator molecule to flow from its initial site to the detector allowing a greater degree of interaction with the sample; but increasing the time to result.

Techniques to minimise variation in capillary height are well known in manufacturing of diagnostic disposable elements. Generally the capillary is formed by a lamination process where an intermediate spacer layer defines the capillary walls and the floor and lid are defined by the base layer and top layer respectively. This approach can be optimised to control capillary height, however particular ways of controlling capillary height to a high degree include use of two layers where a depression is formed in one of the layers itself (rather than using a spacer). This can be achieved by chemical etching, laser ablation, machining or embossing. Alternatively, one of the layers could be formed by a process such as injection moulding, vacuum forming, folding or rolling. Alternatively a precisely controlled height could be achieved by forming a spacer by introducing a hard bead of well-defined diameter, then introducing a filler material around it.

One particular embodiment combines the step where the indicator is coated onto the underside of the lid substrate with a step where the capillary defining spacer layer is also laid down. For example where the indicator is printed onto the substrate in web form by use of a printing process (such as gravure), a subsequent print step, with the web maintained under the same control, could apply one or more thick layers of a dielectric ink that forms the spacer. This has the advantage of improving alignment of the indicator coating to the body of the strip by minimising the number of steps where tolerance errors can accumulate.

An additional source of variability that could apply to the assay formats described above is lateral movement of the test sample fluid after the capillary has been filled. This may occur if the sample introduction is irregular, or if the strip design allows flow through the vent area at the back of the strip, which is required to allow air displacement on sample entry. In order to overcome the irregular fill potential error, the indicator molecule may be located in a defined area on the underside of the lid set back from the sample entry port. This prevents dissolution and diffusion of the indicator molecule before complete fill of the sample chamber.

To prevent the problem of fluid flow after complete fill, a microfluidic dam or capillary stop may be incorporated into the strip. One feature that may particularly be used is to score the capillary floor (by laser or mechanical means) to form a trough perpendicular to the direction of flow at the point in the channel where flow is intended to stop. This scoring acts to provide a morphological barrier to flow and removes high surface energy surface of the capillary, exposing lower surface energy material underneath.

An alternative approach is to create an abrupt change in surface energy at the point in the channel where flow is intended to stop. For example, one or more of the channel surfaces (base, roof or walls) may be substantially hydrophilic throughout the sample chamber to encourage filling, with substantially hydrophobic downstream areas beyond which flow is to be prevented. The hydrophobic area may be created by depositing a hydrophobic material, or by exposing an inherently hydrophobic construction material.

A particular implementation of the configurations described herein is in embodiments where the sample chambers and methods may be implemented using disposable strip and meter technology similar to that in use in existing SMBG systems, providing the benefits of low cost and ease of use.

However, the low cost methods for manufacturing the disposable element may still be utilised to create an appropriate analysis chamber. For example the low cost capillary construction of an SMBG strip could be combined with a Surface Plasmon Resonance based sensor such as Texas Instruments' Spreeta™ liquid analytical sensor.

For some Point of Care diagnostic tests, it may be necessary or advantageous to prepare the sample of physiological fluid in some way before placing it between the indicator source and detector means. For example, plasma may be extracted from a whole blood sample by using a passive filter material (eg glass fibre or polysulfone) upstream from the sample chamber in which the indicator source and detector means are located.

All references referred to above are hereby incorporated by reference.

The invention claimed is:

1. A portable test device for determining a concentration of an analyte in a physiological fluid, the test device having:
   a sample chamber for receiving a sample of the physiological fluid; and, arranged at different locations in the chamber,
      a source of either:
         a predetermined amount of an indicator, or
         an indicator precursor; and
      a detector arranged to measure the flux of said indicator either from the source or from a reaction between said indicator precursor and the fluid,
      wherein the source is located on a first interior side surface of the chamber and the detector is located on an opposite or orthogonal interior side surface of the chamber; and
      wherein the indicator has a specific affinity for said analyte,
      the device being configured such that when the fluid is present in said chamber, a concentration gradient of the indicator is created across said fluid between the source and the detector and the detector measures the flux of said indicator through said fluid, said flux being caused by the concentration gradient and being used to determine the concentration of said analyte.

2. A portable test device according to claim 1 wherein the property to be determined is an inherent property of the fluid and the indicator is chosen so as to have no affinity for any components which are likely to be present in the fluid being tested.

3. A portable test device according to claim 1 further having a processor which is arranged to produce a reading of the property of the fluid from the flux detected by the detector.

4. A portable test device according to claim 1 wherein the sample is substantially static during the measurement of the flux of the indicator.

5. A portable test device according to claim 1 wherein there are a plurality of detectors located at different locations in the chamber, each arranged to measure the flux of said indicator from the source.

6. A portable test device according to claim 5 wherein the source of said indicator is arranged such that each detector is a different distance from said source.

7. A portable test device according to claim 1 wherein there are multiple sources of said indicator arranged at different locations in the chamber.

8. A portable test device according to claim 1 wherein said source includes a plurality of different indicators and at least one detector is arranged to measure the flux of each of said indicators.

9. A portable test device according to claim 1 wherein the chamber has a volume of 5 μL or less.

10. A portable test device according to claim 1 wherein the sample chamber has an entry port and the indicator is located a predetermined distance from the sample entry port.

11. A method of testing, in the portable device of claim 1, the concentration of the analyte in the physiological fluid, the method including the steps of:
   introducing the sample of said fluid to said device;
   creating a concentration gradient across said sample between either:
      a) the source of the indicator, or
      b) an indicator formed as a reaction product of the source of the indicator precursor and the fluid,
      and the detector;
   measuring the flux of said indicator at the detector; and
   determining said property of the physiological fluid from said measurement of the flux.

12. A method according to claim 11 wherein the property to be determined is an inherent property of the fluid and the indicator is chosen so as to have no affinity for any components which are likely to be present in the fluid being tested.

13. A method according to claim 11 wherein the sample is substantially static during the measurement of the flux of the indicator.

14. A method according to claim 11 wherein the sample is not processed prior to introducing the sample to said device.

15. A method according to claim 11 wherein there are a plurality of different indicators and the step of measuring includes measuring the flux of each of said indicators at a detector.

16. A method according to claim 15 wherein the step of determining uses the measurement of the flux of the plurality of different indicators to determine a single property of the physiological fluid.

17. A method according to claim 15 wherein the step of determining uses the measurement of the flux of the plurality of different indicators to determine a plurality of properties of the physiological fluid.

18. A kit for determining a concentration of an analyte in a physiological fluid, the kit comprising:
   a portable test device, the test device having:
      a sample chamber for receiving a sample of the physiological fluid; and, arranged at different locations in the chamber,
      a source of either:
         a predetermined amount of an indicator, or
         an indicator precursor; and
      a detector arranged to measure the flux of said indicator either from the source or from a reaction between said indicator precursor and the fluid,
      wherein the source is located on a first interior side surface of the chamber and the detector is located on an opposite or orthogonal interior side surface of the chamber; and
      wherein the indicator has a specific affinity for said analyte
   the device being configured such that when the fluid is present in said chamber, a concentration gradient of the indicator is created across said fluid between the source and the detector and the detector measures the flux of said indicator through said fluid; and
   a processor for determining the concentration of said analyte fluid from the measurement of said flux, said flux being caused by the concentration gradient.

19. A kit according to claim 18 wherein the property to be determined is an inherent property of the fluid and the indicator is chosen so as to have no affinity for any components which are likely to be present in the fluid being tested.

20. A kit according to claim 18 wherein there are a plurality of detectors located at different locations in the chamber, each arranged to measure the flux of said indicator from the source and the processor is further arranged to determine a property of the fluid from comparison of the measurement of said flux at said plurality of detectors.

21. A kit according to claim 18 wherein said source includes a plurality of different indicators and at least one detector is arranged to measure the flux of each of said indicators.

22. A kit according to claim 21 wherein the processor is arranged to determine a single property of the physiological fluid from the measurement of the flux of the plurality of different indicators.

23. A kit according to claim 21 wherein the processor is arranged to determine a plurality of properties of the physiological fluid from the measurement of the flux of the plurality of different indicators.

24. A kit according claim 18 wherein the chamber has a volume of 5 μL or less.

25. A portable test device according to claim 1 wherein the flux of said indicator is the amount of the indicator reaching a particular area in a unit of time due to diffusion.

26. A kit according to claim 18 wherein the flux of said indicator is the amount of the indicator reaching a particular area in a unit of time due to diffusion.

* * * * *